(12) United States Patent  
Lindsay

(10) Patent No.: US 7,510,562 B2
(45) Date of Patent: Mar. 31, 2009

(54) VEIN DISSECTOR, CAUTERIZING AND LIGATING APPARATUS FOR ENDOSCOPIC HARVESTING OF BLOOD VESSELS

(75) Inventor: Erin Jessica Lindsay, Ann Arbor, MI (US)

(73) Assignees: Terumo Corporation, Shibuya-Ku, Tokyo (JP); Olympus Corporation, Shibuya-Ku, Tokyo (JP)

( * ) Notice: Subject to any disclaimer, the term of this patent is extended or adjusted under 35 U.S.C. 154(b) by 597 days.

(21) Appl. No.: 10/614,183

(22) Filed: Jul. 8, 2003

(65) Prior Publication Data

US 2005/0010242 A1 Jan. 13, 2005

(51) Int. Cl.
*A61B 17/22* (2006.01)
*A61B 17/00* (2006.01)

(52) U.S. Cl. ...................... 606/159; 606/205
(58) Field of Classification Search ................. 606/110, 606/157–159, 169, 170, 206, 99, 205; 600/104–106, 600/159, 235
See application file for complete search history.

(56) References Cited

U.S. PATENT DOCUMENTS

| | | | | |
|---|---|---|---|---|
| 5,282,806 A | * | 2/1994 | Haber et al. | 606/139 |
| 5,306,284 A | * | 4/1994 | Agee et al. | 606/170 |
| 5,352,235 A | * | 10/1994 | Koros et al. | 606/174 |
| 5,569,291 A | * | 10/1996 | Privitera et al. | 606/185 |
| 6,019,771 A | | 2/2000 | Bennett et al. | |
| 6,022,313 A | * | 2/2000 | Ginn et al. | 600/114 |
| 6,193,653 B1 | | 2/2001 | Evans et al. | |
| 6,660,016 B2 | * | 12/2003 | Lindsay | 606/159 |
| 2004/0204275 A1 | * | 10/2004 | Burrowes et al. | 474/263 |
| 2004/0204725 A1 | * | 10/2004 | Bayer | 606/159 |

* cited by examiner

*Primary Examiner*—Todd E Manahan
*Assistant Examiner*—Amy T Lang
(74) *Attorney, Agent, or Firm*—Buchanan Ingersoll & Rooney PC

(57) ABSTRACT

An endoscopic apparatus for harvesting a desired blood vessel including an endoscopic barrel having at least two lumens, one of the lumens dimensioned for receiving an endoscope, a handle disposed at a proximal end of the endoscopic barrel, a cone portion disposed over a distal end of the endoscopic barrel, and at least one manipulator fork extendable from the cone portion for dissecting the desired blood vessel from connective tissue.

14 Claims, 9 Drawing Sheets

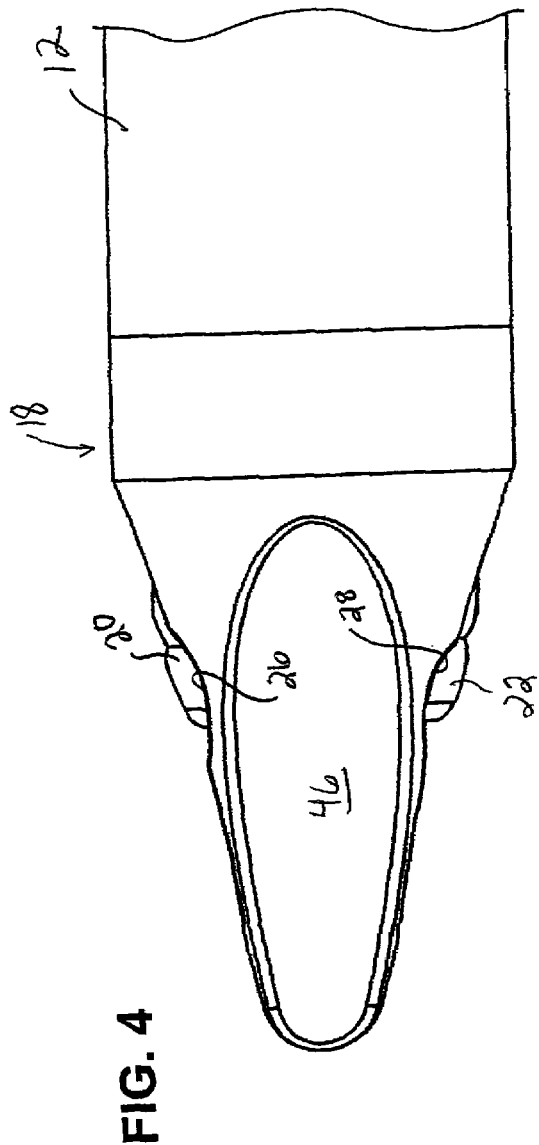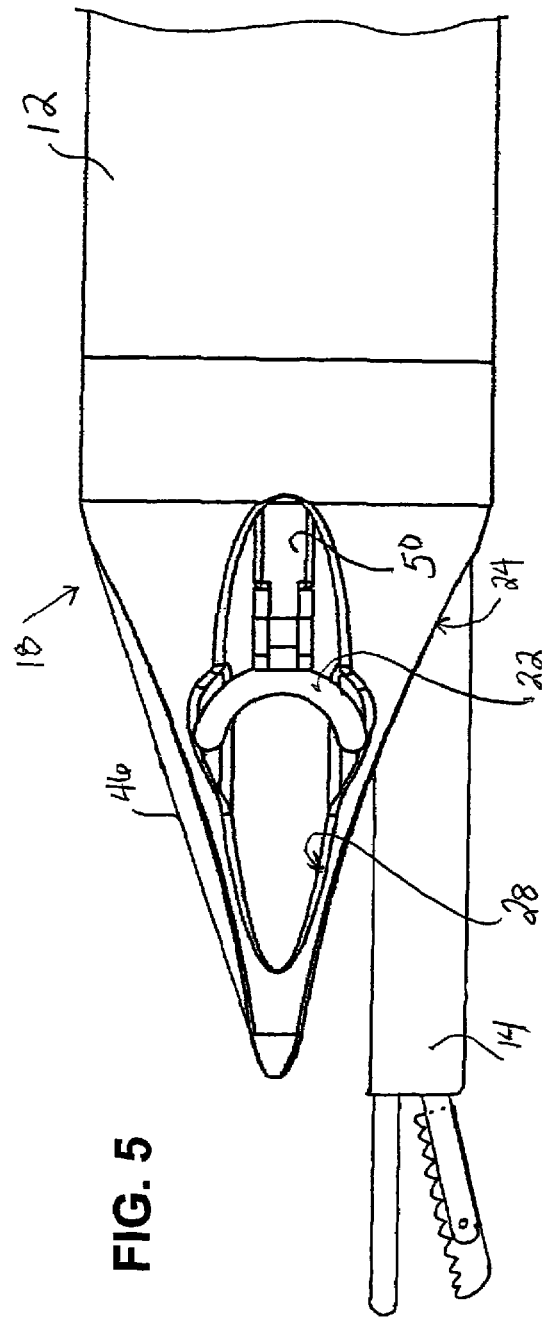
FIG. 4
FIG. 5

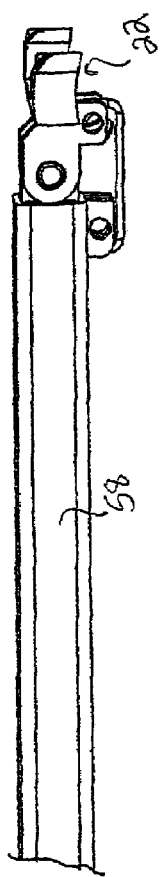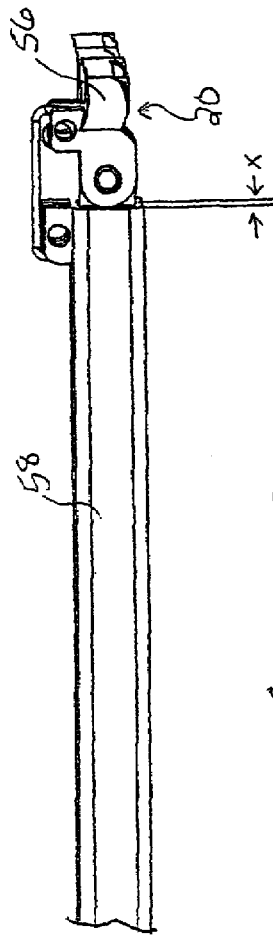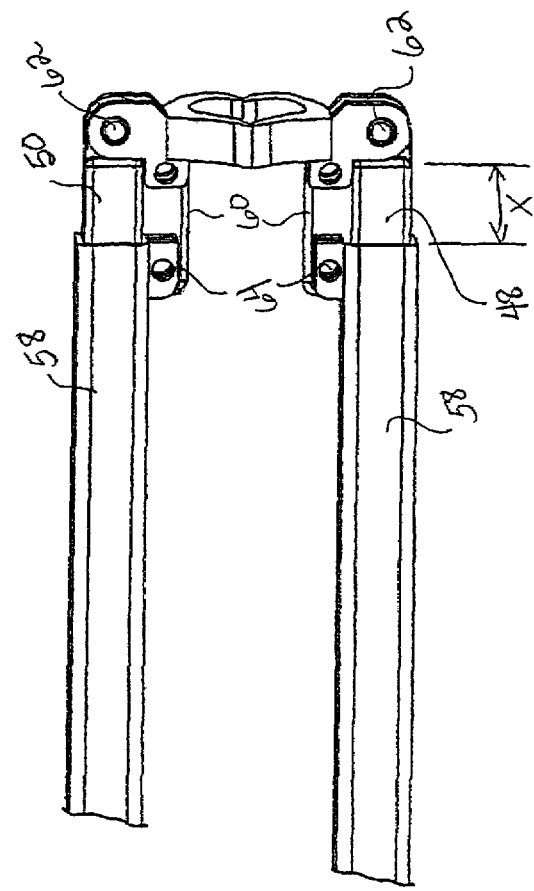
FIG. 7
FIG. 8

VEIN DISSECTOR, CAUTERIZING AND LIGATING APPARATUS FOR ENDOSCOPIC HARVESTING OF BLOOD VESSELS

BACKGROUND OF THE INVENTION

The present invention relates to the harvesting of blood vessels and, more particularly, to methods and apparatus for endoscopic dissection and retraction of sections of blood vessels, such as saphenous veins, for use as a coronary artery bypass graft.

It is common during various surgical procedures, and most particularly during coronary artery bypass grafting (CABG), to remove or "harvest" a blood vessel or vessel section, such as an artery or vein, from its natural location in a patient's body and to use it elsewhere in the body. In CABG surgery, the blood vessel is used to form a bypass between an arterial blood source and the coronary artery that is to be bypassed. Often an artery proximate the heart, such as one of the internal mammary arteries, can be used as the bypass graft, although the saphenous veins in the legs, or a radial artery in an arm can also be used as well.

The conventional surgical procedure used to harvest a section of the saphenous vein, or the like, for use in the CABG surgery, is generally very traumatic to a patient. The procedure involves making a continuous incision in the leg for the full length of the desired vein section in order to provide adequate exposure for visualizing the vein and for introducing surgical instruments to sever, cauterize and ligate the tissue and side branches of the vein. The incision must then be closed by suturing or stapling along its length. Significant complications from this procedure may arise, such as infections, nerve damage, and hematomas. This type of surgical procedure is also known to produce undesirable scarring and can increase the patient's recovery time and hospital stay; thus adding to the overall cost of the CABG procedure.

In an attempt to overcome these problems, less-invasive techniques for harvesting blood vessels have been developed which employ only two small incisions, generally one at each end of the section of vessel to be removed. Primary dissection occurs by introduction of one or more surgical instruments through a first incision to create a working space and separate the vein from the surrounding tissue. Then further instruments are introduced into the generally limited working space to dissect the blood vessel from the connective tissue surrounding the section to be harvested. The side branches of the blood vessel are also clipped and/or cauterized. In order to remove the desired section of the blood vessel, a second small incision, or stab wound, is made at the distal end thereof and the distal end of the blood vessel section is ligated. The proximal end of the blood vessel section is then also ligated, thereby allowing the desired section to be completely removed through the first incision. An endoscopic instrument is generally required for such a procedure to enhance visualization of the vessel and the surrounding tissue and to properly position the surgical instrument. Example of such endoscopic instruments for harvesting blood vessels are shown in U.S. Pat. No. 6,193,653 to Evans et al. and U.S. Pat. No. 6,019,771 to Bennett et al.

These types of less invasive techniques reduce the overall length of the incision, as well as the trauma to the blood vessel section and the surrounding tissue. The introduction of the plurality of surgical instruments through the incision, however, may still cause some damage to the harvested section of the vessel which must then be repaired before it can be used as a graft.

Accordingly, it would be desirable to have a vessel harvesting device and procedure that minimizes the number of surgical instruments that must be inserted into the patient's body and provides for more precise manipulation of the blood vessel by a surgeon.

SUMMARY OF THE INVENTION

The present invention provides an endoscopic apparatus for harvesting blood vessels which has an endoscopic barrel including a plurality of lumens, one of the lumens being dimensioned for receiving an endoscope. A handle is disposed at a proximal end of the endoscopic barrel and a cone portion is disposed over a distal end of the endoscopic barrel. At least one manipulator fork is extendable from the cone portion for dissecting the desired blood vessel from connective tissue.

In a preferred embodiment, the cone portion includes at least one recess for receiving the at least one manipulator fork in a retracted position such that a contoured profile of said portion is maintained.

Still further, the endoscopic apparatus comprises a cutting device extendable from the cone portion for cauterizing and ligating the desired blood vessel and the cone portion further includes a recess for receiving the cutting device in a retracted position such that the contoured profile of the cone portion is maintained.

The at least one manipulator fork includes a control assembly within the handle permitting rotational and translational movement of the at least one manipulator fork. The manipulator fork includes, amongst other components, a fork arm extending from the handle to a distal fork end of each respective manipulator fork such that rotational and/or translational movement of the control mechanism between a first position and a second position produces a predetermined movement of the respective manipulator fork. More preferably, the control assembly further includes a swivel control ring disposed on the handle and permitting swivelling of the distal fork end relative to the fork arm.

DETAILED DESCRIPTION OF THE FIGURES

These, and other objects, features, and advantages of the present invention will become more readily apparent to those skilled in the art upon reading the following detailed description, in conjunction with the appended drawings in which:

FIG. 4 is an enlarged top plan view of the distal end of the vein dissector, cauterizing and ligating apparatus shown in FIG. 2;

FIG. 5 is a side elevational view of the vein dissector, cauterizing and ligating apparatus shown in FIG. 2, with the cauterizing and ligating apparatus shown in an extended position;

FIG. 7 is a top plan view of the manipulator forks in an open position;

FIG. 8 is a top plan view of the manipulator forks in a closed position;

DETAILED DESCRIPTION OF THE PREFERRED EMBODIMENTS OF THE INVENTION

Figure 1:
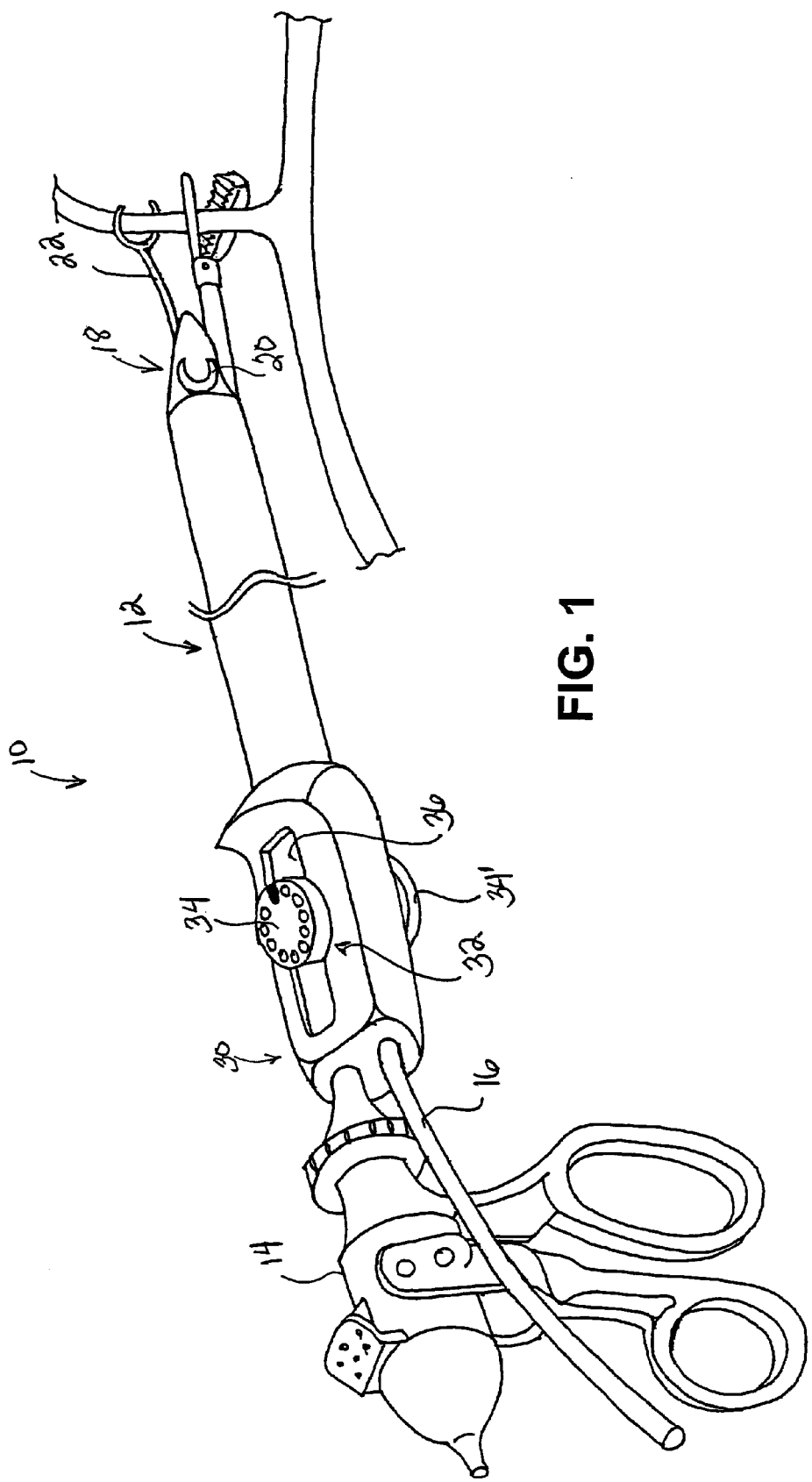
FIG. 1 is a schematic illustration of a vein dissector, cauterizing and ligating apparatus for endoscopic harvesting of blood vessels according to the present invention.

An endoscopic vein dissector, cauterizing and ligating apparatus according to the present invention is shown generally by reference numeral 10 in the schematic illustration of FIG. 1. The vein dissector, cauterizing and ligating apparatus 10 comprises an endoscopic tube 12, a handle portion 30 having a control mechanism 32, and a cone tip portion 18. The endoscopic tube 12 includes a plurality of lumens, preferably four lumens, for receiving therethrough, an endoscope 16, a cauterizing and cutting device 14, and one or more, preferably two, manipulator forks 20, 22. As described in further detail below, the cone tip portion 18 preferably includes a window through which the endoscope obtains a clear field of vision, and recesses for receiving the manipulator forks and cutting device such that these devices may be retracted within their respective recess so as not to disrupt the profile of the cone tip portion. In a preferred embodiment, the cauterizing and ligating device 14 is a ultrasonic device such as the SonoSurg available from Olympus Optical, although other types of devices could also be used. The preferred endoscope 16 of the present invention is a flexible fiberscope.

The extension and retraction of the manipulator forks 20, 22 is preferably operated by a thumb wheel 34 in the handle portion 30, the thumb wheel being slidable within a track 36 to provide the longitudinal extension and retraction of the manipulator forks and fork arms and the thumb wheel being rotatable to obtain the desired rotation thereof. In a preferred embodiment, as described further below, a thumb wheel 34 is provided for control of a first manipulator fork 20 and a second thumb wheel 34' is provided for controlling a second manipulator fork 22.

Figure 2:
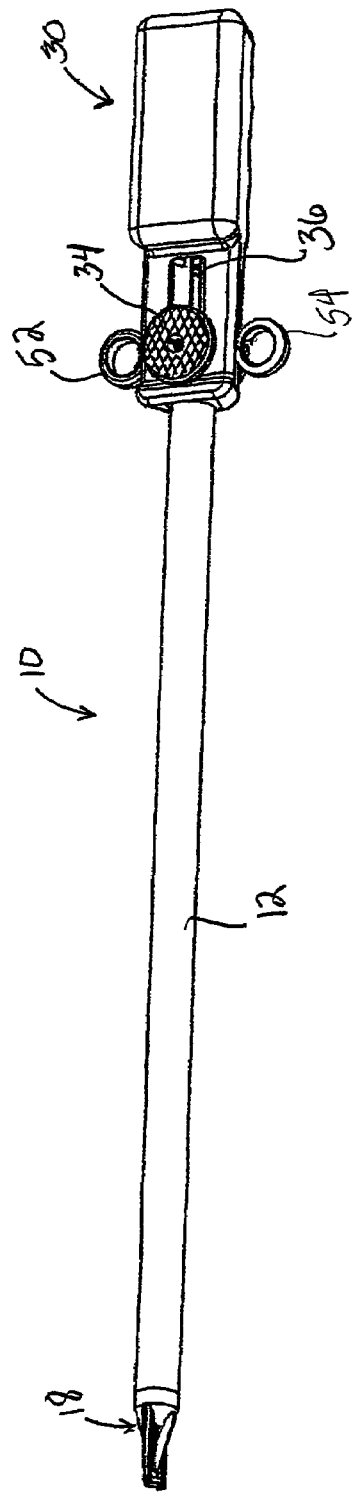
FIG. 2 is a top perspective view of a vein dissector, cauterizing and ligating apparatus according to a preferred embodiment of the present invention.
Figure 3:
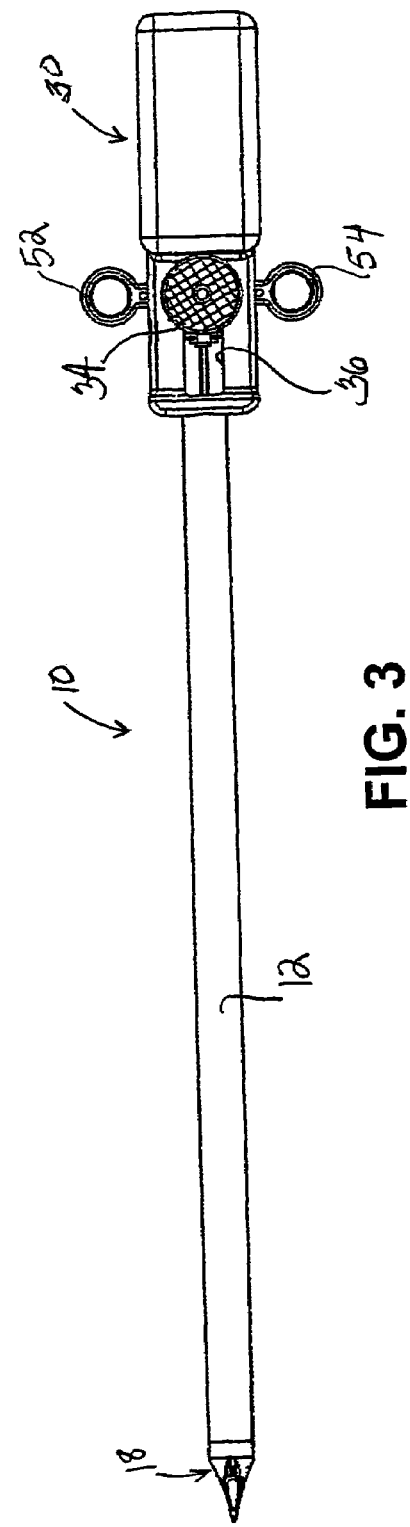
FIG. 3 is a top plan view of the vein dissector, cauterizing and ligating apparatus shown in FIG. 2.

Referring to FIGS. 2 and 3, a preferred embodiment of the apparatus 10 is illustrated wherein the handle portion 30 preferably includes thumb wheels 34, 34', and fork swivel control rings 52, 54. The maximum travel path of the thumb wheels 34, 34' within the respective track 36 is preferably about 50 millimeters. Accordingly, moving the thumb wheel 34 from the rearmost position shown in FIG. 3 to the forwardmost position shown in FIG. 2 will correspondingly extend the manipulator fork 20. In a preferred embodiment, thumb wheel 34 is provided on a top surface of the handle portion 30 for control of fork 20 and thumb wheel 34' is located on the bottom surface of the handle portion 30 for control of fork 22. The thumb wheels are independently slidable within their respective tracks 36, and thus the extension and retraction of the manipulator forks 20, 22 are independent from each other. As explained in greater detail below, each of the thumb wheels 34, 34' includes a plurality of teeth disposed on the underside thereof which engage a pinion gear secured on each of the fork arms. Thus, rotation of the thumb wheel 34, 34' causes the independent rotation of the respective fork arm and manipulator fork 20, 22 disposed on the distal end thereof.

FIGS. 4 and 5 illustrate enlarged views of the cone tip portion 18 of the preferred apparatus 10. The cone tip portion 18 is preferably formed from a transparent material, such as polycarbonate or other suitable material, so as to enable the surgeon to visualize the position of the apparatus 10 through the lens of the endoscope. The cone tip portion 18 further includes a window 46, preferably on the top surface thereof, which maintains the conical profile of the exterior surface of the cone tip portion 18 while protecting the lens of the endoscope 16 positioned therebeneath. The cone tip portion 18 further includes at least one, and preferably two, recesses 26, 28 for receiving the manipulator forks 20, 22. More specifically, the recesses 26, 28 are configured such that with the fork arms 48, 50 retracted and the manipulator forks 20, 22 on the distal ends folded inwardly, the conical profile of the exterior surface of the cone tip portion is not disrupted. The cone tip portion 18 further includes a recess 24 for receiving the cutting device 14. Therefore, the apparatus 10 is utilized with forks 20, 22 and cutting device 14 retracted into the cone tip portion 18 when performing the primary dissection of the tissue from around a section of the desired blood vessel which is to be harvested, and thus creates the working space surrounding the selected section.

Figure 6:
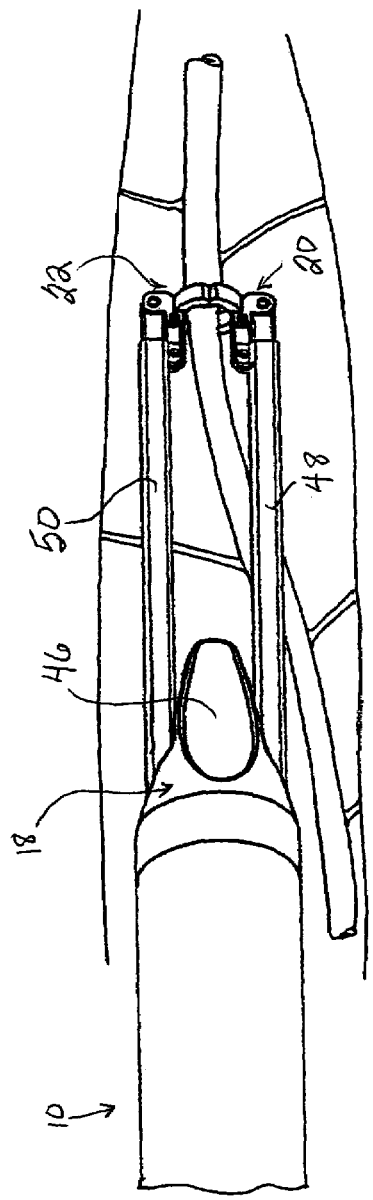
FIG. 6 is a schematic illustration showing the vein dissector, cauterizing and ligating apparatus of FIG. 2, with the manipulator forks in an extended and closed position about a vein.
Figure 13:
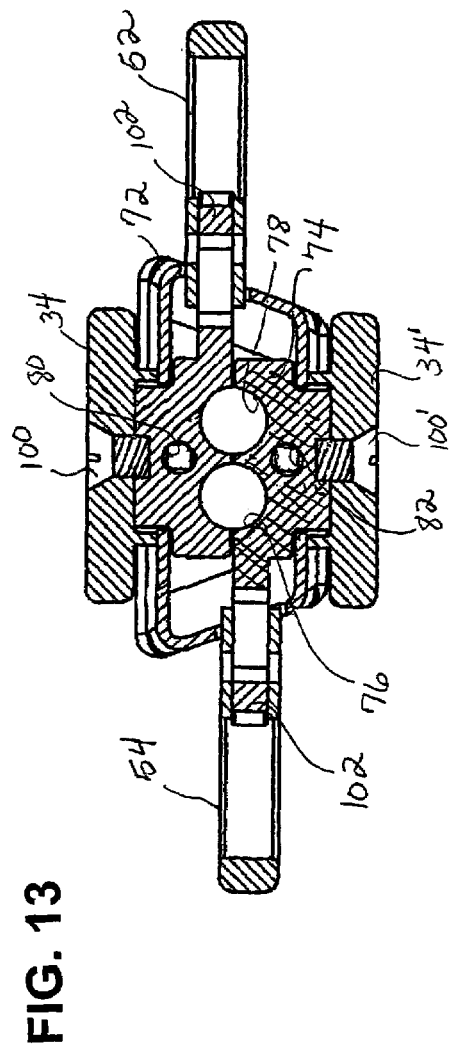
FIG. 13 is a cross-sectional view taken generally along the line 13-13 shown in FIG. 3.

Referring also to FIG. 6, the apparatus 10 is shown in use as it would be for removing connective tissue from the vein to be harvested. As shown, the fork arms 48, 50 are in an extended position and the manipulator forks 20, 22 are swivelled to form a circle around the target vein. FIG. 6 further illustrates the working cavity that is created to surround the vein during the primary dissection utilizing the cone tip portion 18 and, preferably, using carbon dioxide gas insufflation to maintain the expanded cavity. As shown, the protective window 46 guards the lens of the endoscope 16 and provides a clear line of sight to the manipulator forks.

Referring to FIGS. 7 and 8, the manipulator forks 20, 22 are shown in a full open and full closed position, respectively. As explained in further detail below, the fork arms 48, 50 operate independently with respect to extension, rotation, and swivelling or opening and closing of the manipulator forks 20, 22. Of particular note, the manipulator forks 20, 22 include a contour fork surface 56 such that when the fork arms are retracted the outer surface of the fork will blend into the conical profile of the distal end of the apparatus. Each of the fork arms 48, 50 includes a fork swivel control tube 58 which is indexed to the respective fork arm, a fork swivel pin 62 connecting the distal end of the fork arm to the manipulator fork itself, and a fork link 60 held by a lug 64 that extends between the fork swivel control tube 58 and the fork swivel pin 62. Hence, as shown in FIG. 7, when the manipulator forks are in an open position the distal end of the fork swivel control tubes 58 is proximate the fork swivel pin 62 and the distance between the distal end of the control tube 58 and the fork arm 48, 50 is very slight, as denoted by reference "x". Similarly, in the fully closed position when the fork swivel tube 58 is longitudinally translated proximally over the respective fork arm 48, 50, the distance between the distal end of the control tube 58 and the distal end of the fork arm has increased, as denoted by reference "X", and in so doing the manipulator forks have rotated or swivelled approximately 90° inwardly.

Figure 9:
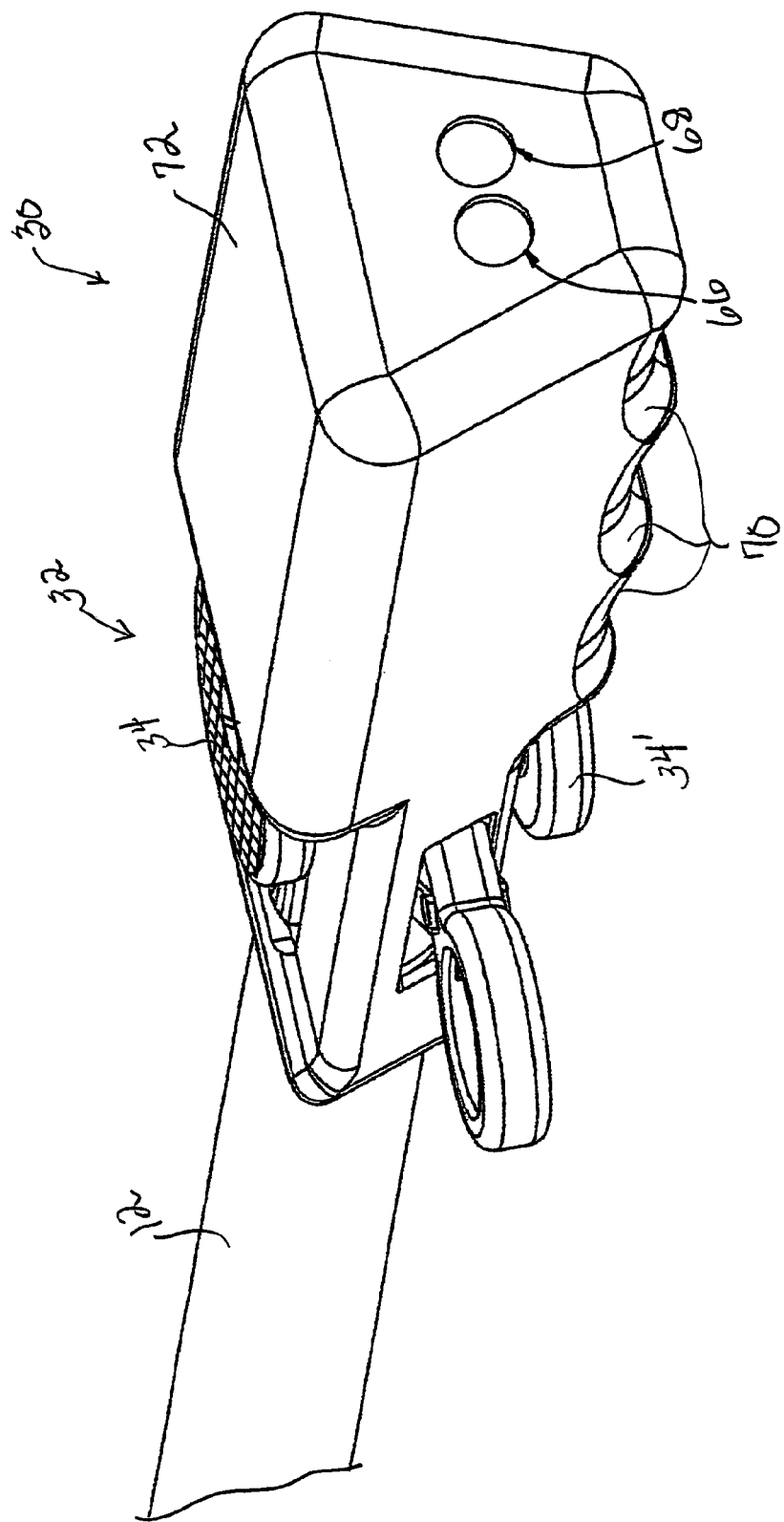
FIG. 9 is a rear perspective view of a handle for the vein dissector, cauterizing and ligating apparatus of FIG. 2.
Figure 10:
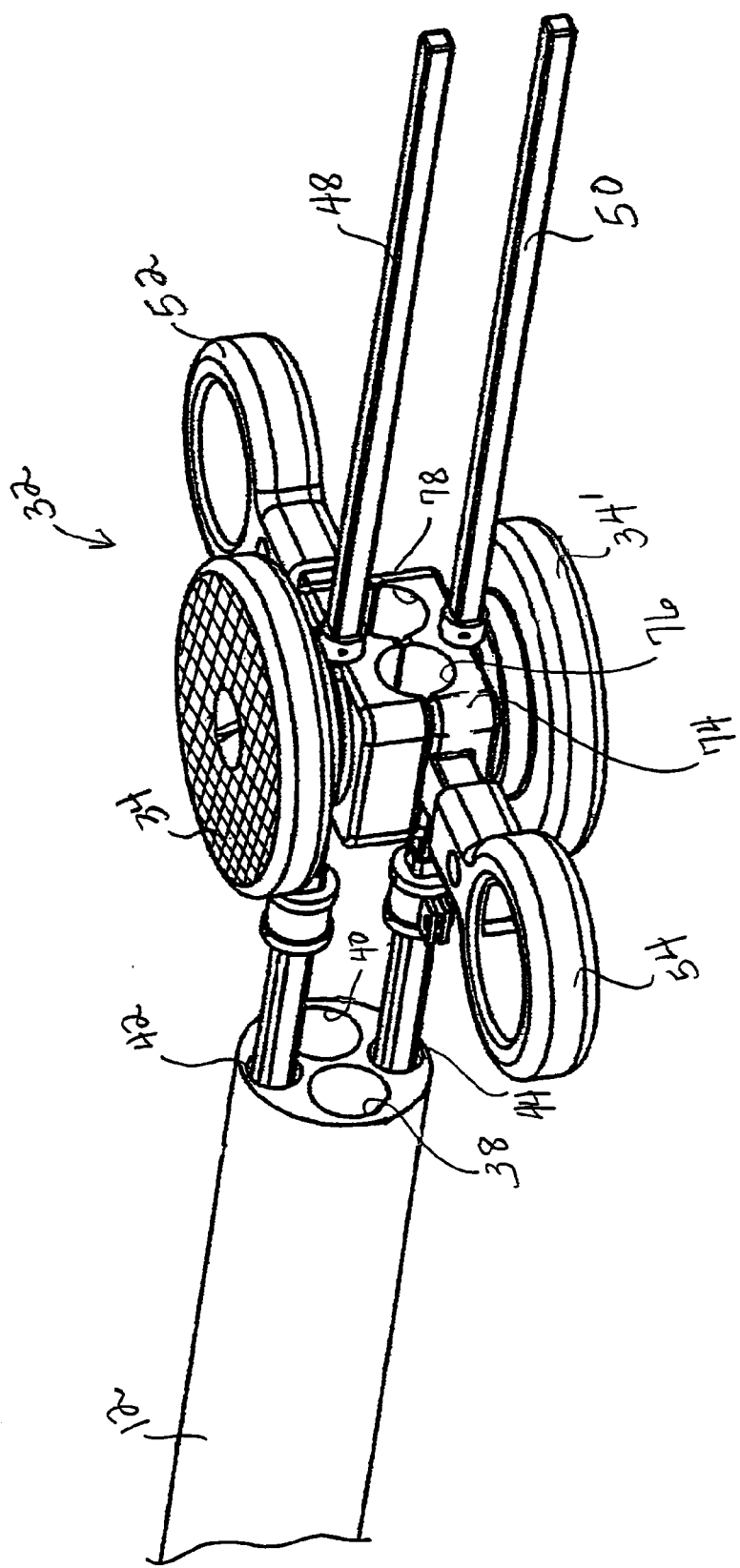
FIG. 10 is a further rear perspective view thereof with the housing of the handle removed for clarity.
Figure 11:
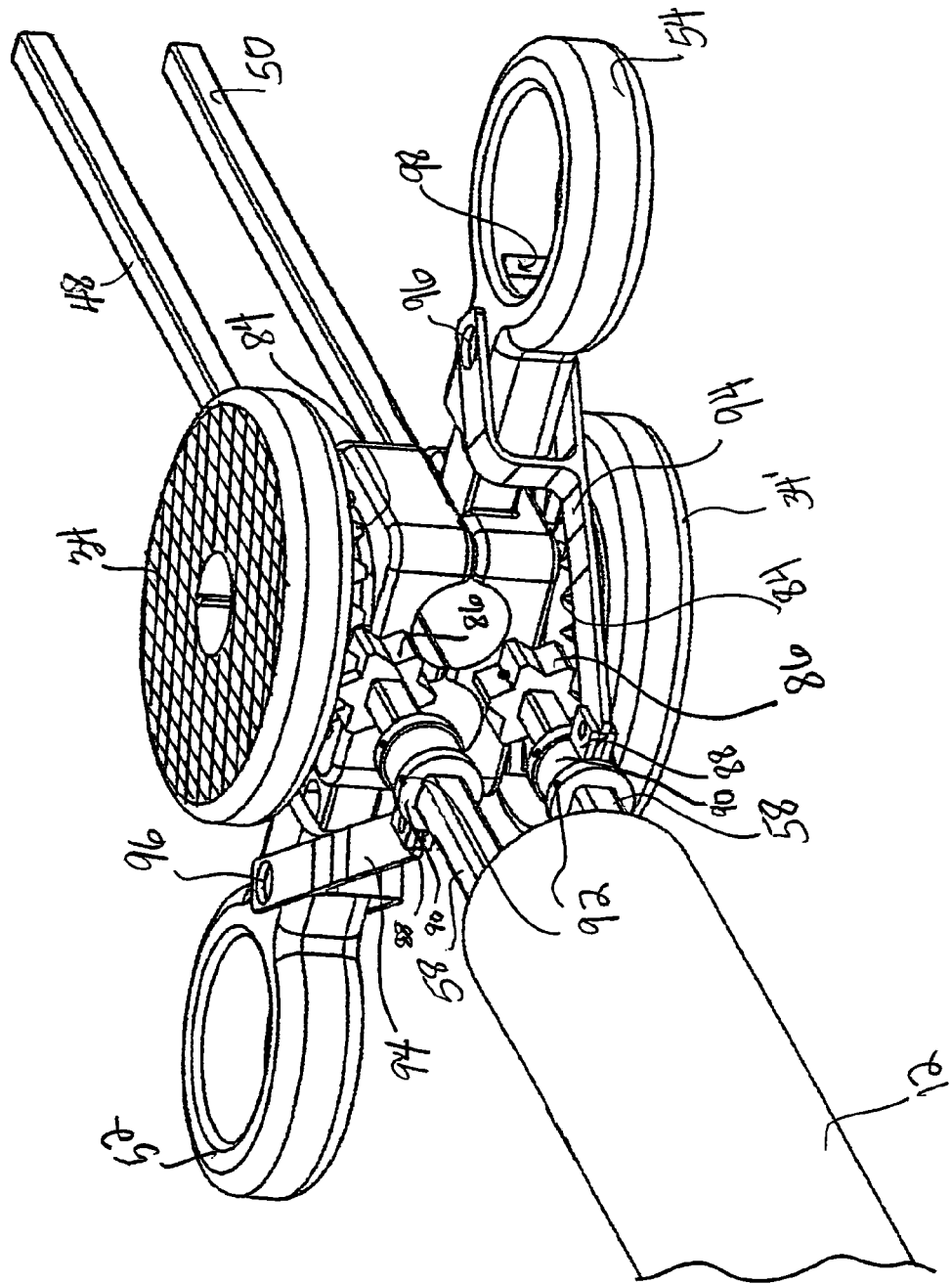
FIG. 11 is a front perspective view of the control mechanism shown in FIG. 10.
Figure 12:
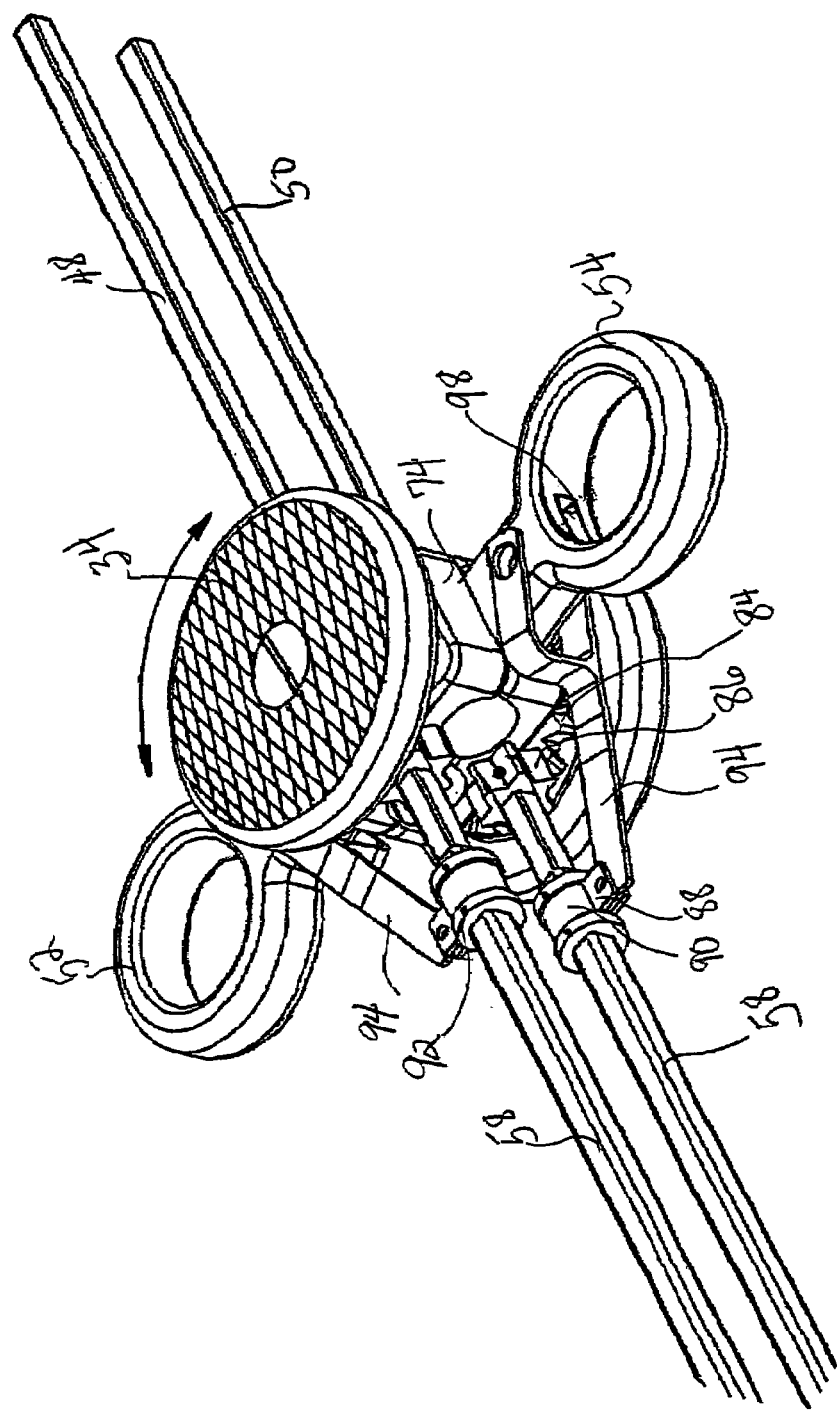
FIG. 12 is a further front perspective view thereof.

The handle portion 30 of the apparatus 10 is shown in greater detail in FIGS. 9-13. As shown in FIG. 9, the handle portion 30 includes a housing 72 having two openings 66, 68 formed therein. As schematically illustrated in FIG. 1, one of the openings is utilized for the endoscope 16 and the other of the openings is utilized for the cauterizing and cutting device 14. Referring to FIGS. 10 and 11, the housing 72 has been removed for clarity, and in FIG. 12 the endoscopic tube 12 has also been removed for clarity. As most clearly shown in FIG. 10, the endoscopic tube 12 preferably includes four lumens. A lumen 38 is preferably provided for receiving the endoscopic imaging system or endoscope 16, the lumen 40 is preferably provided for receiving the selected cauterizing and cutting device 14, the lumen 42 is provided for receiving the right side fork arm 48, and the lumen 44 is provided for receiving the left side fork arm 50.

The fork and arm control mechanism 32 comprises an arm saddle 74 including openings 76 and 78 for receiving the endoscope 16 and the cutting device 14, respectively, and openings 80 and 82 for receiving the right and left fork control arms 48, 50, respectively. A thumb wheel 34, 34' is provided for rotational and translational control of each of the fork arms 48, 50. As illustrated in the preferred embodiment, and best shown in FIG. 13, the thumb wheel 34 is disposed on an upper surface of the housing 72 and retained with a screw 100 and the thumb wheel 34' is disposed on a lower surface of the housing 72 and secured with a screw 100'. Each of the thumb wheels 34, 34' include a plurality of teeth 84 disposed on the underside thereof. The teeth 84 of the thumb wheel engage a pinion gear 86 secured on each of the fork arms 48, 50 and thus rotation of the thumb wheel 34, 34' causes the rotation of the respective fork arm 48, 50 and manipulator fork 20, 22 disposed on the distal end thereof.

In order to obtain the desired opening and closing of the manipulator forks 20, 22, as described above, the arm and fork control mechanism 32 further includes fork swivel control rings 52, 54. The fork swivel control rings 52, 54 extend into and move with the arm saddle 74. Each of the rings includes a slot 98 for receiving a slider stalk 102 extending from the saddle 74. The fork swivel control rings 52, 54 are connected to the respective fork swivel control tube 58 by a fork swivel linkage 94 secured to the respective ring by a retainer pin 96 and secured to the respective control tube 58 by a fork saddle 88 and saddle retention collar 90. The ring retainer and the slider stalk 102 have slots which allow the rings 52, 54 to be moved in a limited path of travel into and away from the arm saddle 74. As such, when the rings are pressed fully together, i.e., moved inwardly toward the arm saddle 74, each of the respective fork swivel control tubes 58 will in turn be moved proximally relative to the respective fork control arm 48, 50, and in so doing the distance between the distal end of the fork arms and the fork swivel control tubes will increase and the manipulator forks 20, 22 will swivel approximately 90°. A lesser degree of swivel can of course also be obtained merely by limiting the distance in which the rings 52, 54 are moved.

After performing the primary dissection, it is not necessary to remove the apparatus through the first incision in order to remove the cone tip portion, as in the prior art devices. As best shown in FIGS. 6-8, each of the manipulator forks 20, 22 is capable of movement within an approximately 90° range. The swivel movement of each of the fork manipulators 20, 22 is independently controlled by the respective fork swivel control ring 52, 54 and the rotational and translational movement of the each of the fork arms 48, 50 is similarly independently controlled by the respective thumb wheel 34, 34'. Thus, during dissection to remove the connective tissue, the manipulator forks 20, 22 may be separated with the manipulator forks in the full open position shown in FIG. 7, for example, so as to enable the vein to be disposed there between. Because the endoscope is preferably positioned above and to the rear of the manipulator forks 20, 22, the optical lens of the endoscope 16 can clearly view the manipulator forks and the tissue to be dissected; thereby providing optimal observation for guiding and operating the apparatus 10. In this manner the manipulator forks 20, 22 can dissect the vein from the connective tissue and the cutting device 14 can cut any side branches along the vein simply by operating the given control mechanism therefor. After removing the side branches and connective tissue, the apparatus 10 may also be used for ligating the distal end of the section of the vein to be harvested. The manipulator forks 20, 22 can be used for properly positioning the vein and the cutting device 14 can once again be used for ligation and cutting of the distal end of the vein. After ligation and cutting of the distal end of the desired blood vessel section, the apparatus 10 may then also be used to ligate and cut the proximal end of the section, thereby allowing the desired section of the vein to be pulled through the first small incision.

The present invention has now been described with reference to a preferred embodiment thereof. The foregoing detailed description has been given for clarity and understanding only. No unnecessary limitations are to be understood therefrom. It will be apparent to those skilled in the art that many changes can be made in the embodiments described without departing from the true scope of the invention. Thus the scope of the present invention should not be limited to the exact details and structures described herein, but rather by the structures described by the language of the claims, and the equivalent thereto.

What is claimed is:

1. An endoscopic apparatus for harvesting a desired blood vessel comprising:

an endoscopic barrel including at least two lumens, one of said lumens dimensioned for receiving an endoscope;

a handle disposed at a proximal end of the endoscopic barrel;

a cone portion fixedly secured to and integral with a distal end of said endoscopic barrel, said cone portion having an interior surface facing the distal end of said endoscopic barrel and a conical exterior surface facing outwardly from the apparatus, said conical exterior surface being defined by a base ring having a circular circumference and a plurality of side portions tapering toward a vertex and forming a pointed distal end of said cone portion; and at least one manipulator fork arm having a manipulator fork disposed on the distal end thereof, said manipulator fork arm being extendable through an opening in said integral cone portion for dissecting the desired blood vessel, wherein said cone portion includes at least one fork recess in the conical exterior surface for receiving and maintaining said at least one manipulator fork against the exterior surface of said cone portion when said at least one manipulator fork is fully retracted so as to preserve a smooth profile of the exterior surface of said cone portion between the circular base and the pointed distal end, said at least one fork recess not allowing said at least one manipulator fork to pass through the opening of said cone portion when in a fully retracted position.

2. The endoscopic apparatus of claim 1, wherein said endoscopic barrel includes at least three lumens and said apparatus further comprises a cutting device extendable from said cone portion for cauterizing and ligating the desired blood vessel.

3. The endoscopic apparatus of claim 2, wherein said cone portion further includes a cutting device recess in the distal exterior surface for receiving said cutting device when in a retracted position such that a contoured profile of said portion is maintained.

4. The endoscopic apparatus of claim 1, wherein said at least one manipulator fork includes a control assembly permitting rotational and translational movement of said at least one manipulator fork.

5. The endoscopic apparatus of claim 4, wherein said control assembly comprises a rotatable control mechanism slidable within a predefined track on said handle.

6. The endoscopic apparatus of claim 4, wherein said control assembly further permits swivelling of said distal fork relative to said fork arm.

7. The endoscopic apparatus of claim 6, wherein said at least one manipulator fork further comprises a fork swivel control tube disposed over said fork arm.

8. The endoscopic apparatus of claim 7, wherein said control assembly further includes a swivel control ring disposed on said handle.

9. The endoscopic apparatus of claim 1, wherein said endoscopic barrel includes at least three lumens and at least two manipulator forks.

10. The endoscopic apparatus of claim 1, wherein a line drawn from said vertex to a plane of said circular base ring is perpendicular to the plane of said circular base ring.

11. An endoscopic apparatus for harvesting a desired blood vessel comprising:
  an endoscopic barrel including at least two lumens, one of said lumens dimensioned for receiving an endoscope;
  a handle disposed at a proximal end of the endoscopic barrel;
  a cone portion integral with said endoscopic barrel, said cone portion having a conical exterior surface facing outwardly from the apparatus, said conical exterior surface being defined by a circular base ring and a plurality of side portions tapering toward a vertex forming a pointed distal end of said cone portion; and
  at least one manipulator fork arm extendable through an opening in said cone portion said at least one fork arm having a manipulator fork disposed on a distal end thereof, said manipulator fork being maintained against an exterior surface of said cone portion when in a fully retracted position so as to preserve a smooth profile of the exterior surface of said cone portion between the circular base ring and the pointed distal end, and disposed exterior to said cone portion when dissecting the desired blood vessel;
  wherein said cone portion is fixedly secured to a distal end of the endoscopic barrel during harvesting of a desired blood vessel.

12. The endoscopic apparatus of claim 11, wherein said endoscopic barrel includes at least three lumens and said apparatus further comprises a cuffing device extendable through said cone portion for cauterizing and ligating the desired blood vessel.

13. The endoscopic apparatus of claim 11, wherein said endoscopic barrel includes at least three lumens and at least two manipulator forks.

14. The endoscopic apparatus of claim 11, wherein a line drawn from said vertex to a plane of said circular base ring is perpendicular to the plane of said circular base ring.

* * * * *